(12) United States Patent
Knoche et al.

(10) Patent No.: US 7,491,956 B2
(45) Date of Patent: Feb. 17, 2009

(54) OPTICAL SCANNING DEVICE HAVING A DISTANCE SENSOR AND A DETERMINED FOCAL DISTANCE FOR SCANNING OBJECTS

(75) Inventors: Jochem Knoche, Erlangen (DE); Sebastian Schmidt, Weisendorf (DE); Christian P. Schultz, Beverly, MA (US); Wolfgang Strob, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 25 days.

(21) Appl. No.: 11/699,722

(22) Filed: Jan. 29, 2007

(65) Prior Publication Data

US 2007/0239034 A1    Oct. 11, 2007

(30) Foreign Application Priority Data

Feb. 1, 2006    (DE) .................. 10 2006 004 583

(51) Int. Cl.
*G01N 21/86* (2006.01)
(52) U.S. Cl. .................. 250/559.29; 250/208.1
(58) Field of Classification Search ............ 250/559.29, 250/559.3, 559.38, 559.4, 221, 235, 458.1, 250/461.1, 459.1, 201.2, 208.1; 600/135, 600/184, 476; 235/462.2, 462.23; 356/399–402
See application file for complete search history.

(56) References Cited

U.S. PATENT DOCUMENTS 5,216,230 A * 6/1993 Nakazawa .................. 235/454
6,783,068 B2 * 8/2004 Hecht ........................ 235/435

FOREIGN PATENT DOCUMENTS

| DE | 25 37 482 | 3/1977 |
| DE | 101 32 624 A1 | 1/2002 |
| WO | WO 9603708 A1 | 2/1996 |
| WO | WO 01/22870 A1 | 4/2001 |

OTHER PUBLICATIONS

German Office Action for DE 10 2006 004 583.1-51 dated Oct. 2, 2006 in English.

* cited by examiner

*Primary Examiner*—Que T Le
(74) *Attorney, Agent, or Firm*—Brinks, Hofer, Gilson & Lione

(57) ABSTRACT

An optical scanning device is provided. The optical scanning device an excitation light source that is operable to illuminate the object to be scanned. An image detector is operable to detect excited emission rays through illumination of the object to be scanned by the excitation light source and imaging optics that dictate a focal distance. The image detector detects a scan image of the emission radiation of the object to be scanned with the highest level of image sharpness if the focal distance is maintained. A control device includes a distance sensor through which a distance between an optical scanning device and the object to be scanned can be measured, wherein maintenance of the focal distance as the function of the measured distance can be checked by the control device.

20 Claims, 2 Drawing Sheets

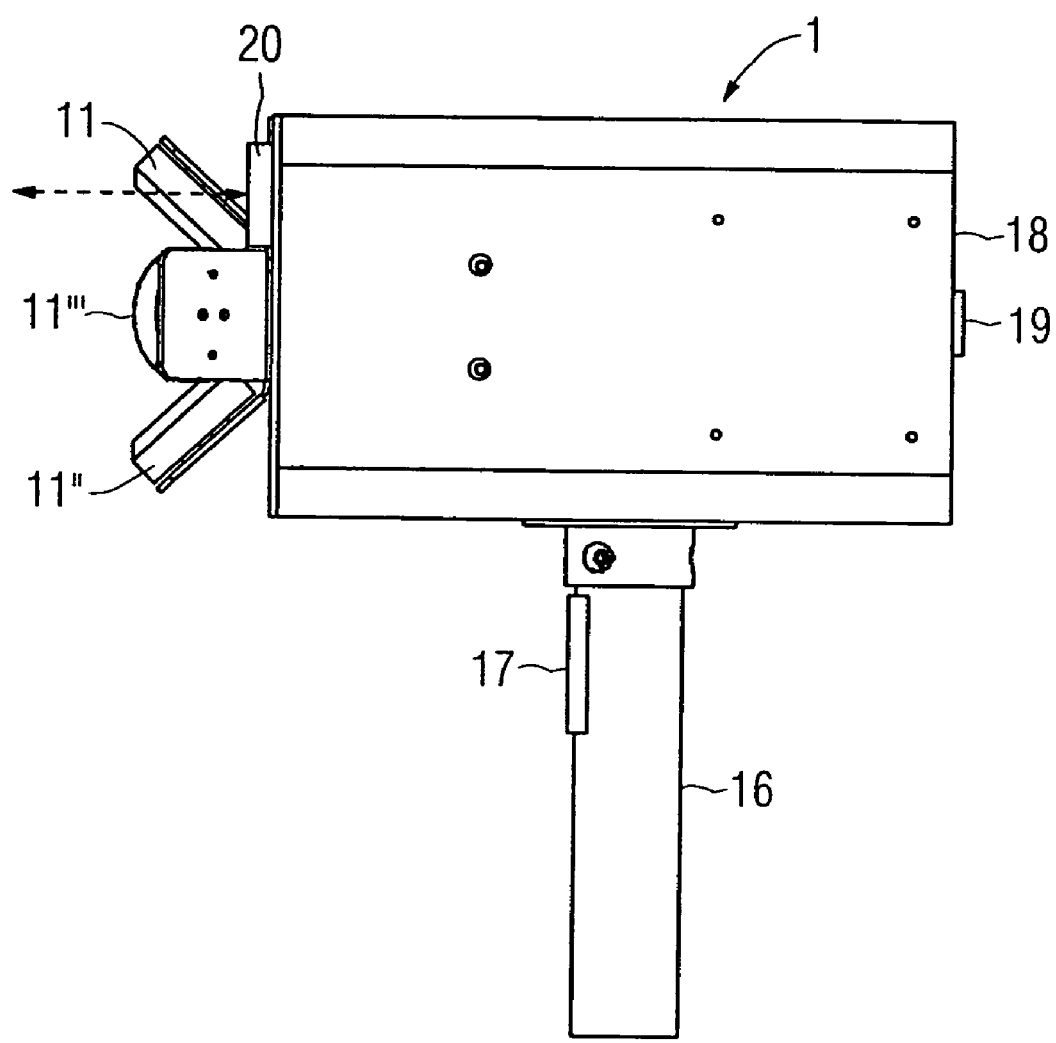

OPTICAL SCANNING DEVICE HAVING A DISTANCE SENSOR AND A DETERMINED FOCAL DISTANCE FOR SCANNING OBJECTS

The present patent document claims the benefit of the filing date of DE 10 2006 004 583.1, filed Feb. 1, 2006, which is hereby incorporated by reference.

BACKGROUND

Optical scanning devices that operate based on electromagnetic radiation or visible light may be used for scanning material, tissue, or substance properties, for example, surface properties, roughness, absorption behavior, transparency, optical characteristics not perceptible or barely perceptible to the human eye, fractures, cracks, or material deposits.

Medical diagnostics optical scanning devices based on visible light and additional light of an infrared or other suitable wavelength may be used to scan human or animal tissue. The optical light-based scan allows an optical image to be reconstructed and visualized, whereas scanning based on infrared or other suitable light makes it possible, for example, to examine tissue, which is treated beforehand with markers, for the presence of diseases such as cancer. Marked diseased tissue shows fluorescence occurrences in such cases. The method is also referred to as fluorescence scan or fluorescence detection. The scanned image that is created is referred to as a fluorescence scan or fluorescence image.

In addition to the fluorescence characteristics, luminescence characteristics or further optical emission occurrences can also be detected in the same manner. In the following description, the term fluorescence will be used, but may include the further luminescence or emission occurrences in each case.

An apparatus for fluorescence detection, which may be referred to as a fluorescence scanner, can be used to detect a wide range of molecular characteristics because substances with different molecular characteristics exhibit different fluorescence characteristics, which can be explicitly detected. Fluorescence detection is optically based and is non-invasive or is only minimally invasive.

Fluorescence methods are used for examinations of areas close to the surface of the body or examinations of the body opened during an operation (intraoperative applications). Examples of such examinations are the detection of fluorescently marked skin cancer or the detection of tumor boundaries in the resection of fluorescently marked tumors. The company NOVADAQ has developed a system to make intraoperative coronary arteries and the function (i.e. the through-flow) of bypasses visible.

Medical diagnosis molecular characteristics commonly referred to as a "molecular signature," for example, give information about the state of health of a living thing or patient. The molecular signature may be evaluated diagnostically. Molecular signatures may be employed for the detection of cancer. The molecular signature can also be used to identify other symptoms, such as rheumatoid arthritis or arteriosclerosis of the carotic artery.

Generally, fluorescence detection requires that the fluorescence be excited, which can be done in a simple manner by optical excitation. The excitation light can lie in the infrared range (IR) or in the near infrared range (NIR). A suitable frequency range depends on the substance to be examined. Substances that do not themselves have any molecular or chemical characteristics, which would be suitable for fluorescence detection, can be molecularly "marked" in a suitable manner. For example, markers can be used that, with appropriate preparation, bind or attach themselves to specific molecules. This type of marking functions according to a mechanism which can be illustrated as a key-lock mechanism.

In key-lock mechanisms, markers and molecules to be verified fit into each other like a key in a lock. The marker does not bind to other substances. If the marker exhibits known fluorescence characteristics, it can be optically detected after binding or attachment. The detection of the marker allows the presence of the marked specific substance to be confirmed. Detection only requires one image detector, which is capable of detecting the light in that wavelength that the substance or the marker used emits on excitation.

Fluorescent metabolic markers, which accumulate exclusively in specific regions (e.g. tumors, inflammations or other specific seats of disease) or are distributed throughout the body but are only activated in particular regions, for example, by tumor-specific enzyme activities (and through additional irradiation by light for example), are an object of research in biotechnology.

What are referred to as fluorophores are known as marker substances, for example, indocianine green (ICG). The marker substances, for example, bind to vessels and are optically verifiable. In an imaging method, the contrast with which vessels are displayed can be increased. "Smart contrast agents" are becoming increasingly important. Smart contrast agents are activatable fluorescence markers that, for example, bind to tumor tissue and the fluorescent characteristics that are only activated by binding to the material to be marked. These types of substance may include self-quenched dye media, for example, Cy5.5, which are bound to larger molecules via specific peptides. The peptides can be detected and split up by specific proteases, which are produced in tumors, for example. The splitting up releases the fluorophores and they are then no longer self-quenched but develop their fluorescent characteristics. The released fluorophores can, for example, be activated in the near IR wavelength range around 740 nm. One example of a marker on this basis is AF 750 (Alexa Fluor 750) with a defined absorption and emission spectrum in the wavelength range of 750 nm (excitation) or 780 nm (emission).

In medical diagnosis these types of activatable markers may be used, for example, for intraoperative detection of tumor tissue to enable the diseased tissue to be identified and then removed. A typical application is the surgical treatment of ovarian cancer. The diseased tissue may be surgically removed and subsequently treated using chemotherapy. The increased sensitivity of fluorescence detection increases the ability to detect the diseased tissue along with various surrounding foci of disease and remove the disease more completely.

The detection of a fluorescently marked region includes irradiating the region with the light in the specific excitation wavelength of the fluorescence dye and detecting the emitted light in the corresponding emission wavelength of the fluorophore. A fluorescence scan is created by recording a fluorescence image based on fluorescent light.

If the fluorescence exhibits a low luminous intensity or lies in a wavelength range not visible to the human eye, an additional visualization of the fluorescent tissue areas is necessary. An optical image based on visible light is recorded. Optical and fluorescence image are reproduced superimposed (fused) in order to display the fluorescence within the context of the optical image. The fused image with the fluorescently marked tissue is displayed on a screen of the fluorescence scanner or at an external computer with image processing software.

Users are enabled by the shared reproduction of the optical and the scanning information to orient themselves initially, as regards proportion and position, to the optically reproduced body or object in the display and then transfer the scan information to the real scenario. The surgeon can, for example, detect the tumor tissue on the screen and subsequently locate the tumor tissue in the body of the patient.

To record both an optical and a fluorescence image, a beam splitter may be provided. The beam splitter splits the beam of light coming from the object or body to be examined into a beam that has a spectrum that lies in the wavelength range of the fluorescence and a further beam in the visible wavelength range. The IR or NIR beam is guided to an image detector provided especially for the IR or NIR beam, and the visible beam is guided to a suitable image detector.

Instead of the above splitter, a filter changer can also be arranged in the path of the beam in front of the image detector. The filter changer swaps in a separate filter in each case for recording fluorescence images and for recording optical images. A filter, which filters out the light in the visible wavelength range, must at least be provided for the fluorescence images, since otherwise the fluorescent light would be outshone.

The fluorescent light may lie in the infrared wavelength (IR) range or in the near infrared (NIR) range. Excitation light of a suitable wavelength is only able to be produced at sufficient intensity with a comparatively low efficiency using current lighting devices. Because of the low efficiency, the heat generated is generally large and the energy expended to create the excitation light is considerable.

To reduce heat generation and energy outlay, operation of the fluorescence scanner in an automatically pulsed mode is known. The pulsed mode records images in rapid succession based on visible light and based on fluorescent light.

A shutter with a large aperture is generally provided in the optics of the fluorescent scanner to increase the light sensitivity because of the low luminous intensity of fluorescent light. Although the large aperture increases the light sensitivity, the depth of field obtainable (that is the focal distance range within which it is possible to record an image in sharp focus) is reduced. The fluorescence scanner must be held exactly at a distance from the surface dictated by the focal distance (that is the respective distance which, if maintained, enables the greatest sharpness of the image) to enable an image with the greatest possible sharpness to be recorded.

If a therapeutic intervention based on a scan image is to be planned, a high image quality and resolution are indispensable. If such procedures involve medical intervention on living tissue, an additional factor rendering this situation more difficult can be the tissue's own movement.

SUMMARY

The present embodiments may obviate one or more of the drawbacks or limitations of the related art. For example, in one embodiment, an optical scanning device, for example, a fluorescence scanner is able to be positioned at a distance from an object or a body to be scanned predetermined by the focal distance of the scanning optics.

In one embodiment, an optical scanning device includes an excitation light source, which is arranged to illuminate an object to be scanned; an image detector, which is embodied to detect emission of radiation of the object to be scanned excited by the excitation light source; and imaging optics, which dictate a focal distance and when maintained enable the image detector to detect a scanned image of the emission radiation of the object to be scanned with the greatest image sharpness. A control device includes a distance sensor. The distance sensor is operable to measure the distance between the optical scanning device and the object to be scanned. The control device is operable to check and maintain the focal distance as a function of the measured distance. The checking by the control device of the maintenance of the focal distance provides support for a user in recording scanned images with high image sharpness. This support allows the user to devote more attention to activities or aspects other than maintaining the focal distance.

In one embodiment, the control device is operable to suppress triggering of the detection of a scanned image. The unnecessary detection of scanned images with a sharpness less than the highest possible image sharpness may be prevented. The energy required to create a scanned image, especially to create excitation light, can be saved. Energy consumption may be important in mobile battery-operated scanning devices. An unnecessary data transmission to outside equipment may also be avoided, helping to save both transmission bandwidth and also energy. A user is spared having to record a plurality of scanned images, checking the sharpness and if necessary recording new images. Because the user only needs to record a single scanned image in each case and because a high level of sharpness is ensured in each case by the control device, a saving in time and effort is achieved.

In one embodiment, the control device may suppress storage of a scanned image. In this embodiment, the unnecessary storage of scanned images with a sharpness less than the highest possible sharpness may be prevented. The storage space required for storing scanned images may be reduced, which is of particular advantage with a mobile scanning device with limited memory resources. In addition a subsequent manual editing of the memory content, for example, by deleting images which are not sharp enough, can be dispensed with. This saves a user time and effort.

In one embodiment, the control device includes a distance checking indicator. The distance checking indicator includes a display that may be activated by the control device. The distance checking indicator is able to indicate that the correct distance is being maintained. This makes it possible for a user, even before or during triggering of the recording of a scanned image, to register whether a scanned image with a high level of image sharpness is to be expected. This saves a user having to record a plurality of scanned images, check the sharpness and if necessary make further recordings, for example.

BRIEF DESCRIPTION OF THE DRAWINGS

FIG. 3 is a side view that illustrates one embodiment of a fluorescence scanner.

DETAILED DESCRIPTION

Figure 1:
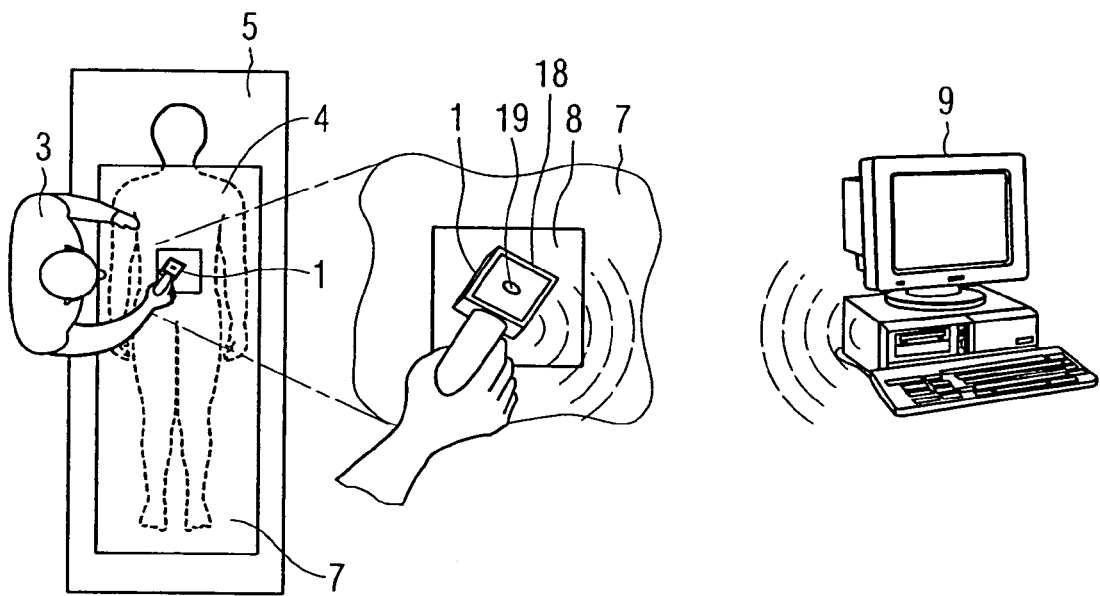
FIG. 1 is a schematic diagram of one application of one embodiment of an optical scanning device.

FIG. 1 shows one application of an optical scanning device embodied as a fluorescence scanner 1. A patient 4 to be examined is covered by an operating (OP) drape 7 and lies on an OP table 5. A surgeon 3 works on a region of the body of the patient 4 through an opening of the OP drape 7. The surgeon 3 holds in his hand a mobile battery-operated fluorescence scanner 1. The scanner 1 allows the surgeon 3 to examine regions of the body to be treated.

The middle part of FIG. 1 illustrates the scan region 8 of the patient 4 to be examined in an enlarged view. In one embodiment, the patient 4 is covered by the OP drape 7 except for an opening in the OP drape 7 over the scan region 8. The surgeon 3 directs the fluorescence scanner 1 centrally onto the scan region 8, which is visible and accessible through the opening.

In one embodiment, data recorded by the fluorescence scanner 1 is transmitted wirelessly to a PC workstation 9. The wireless transmission is illustrated in FIG. 1. In one embodiment, the PC workstation 9 displays the received data of the scan region 8 on the screen. The surgeon 3 may view the fluorescence scan results on the screen of the PC workstation 9. The scan results are immediately available for inspection. If necessary, the surgeon 3 can orient his operation strategy or planning in accordance with the fluorescence scan results.

To allow orientation in the image in one embodiment, the optical presentation of the fluorescence scan is superimposed by a display of the same visible area or the same scan region 8 as a normal image in the visible wavelength range. For example, using the image in the visible wavelength range, the surgeon 3 may recognize details of the scan region 8 on the screen and, using the superimposed fluorescence scan, the surgeon 3 can assign the result of the scan to the actual visible points of the scan region 8. The superimposition of an image recorded in the visible wavelength range may be useful if the fluorescence lies in a non-visible wavelength range, for example, IR.

In one embodiment, the fluorescence scanner 1 includes a display 18 on which the image data of the scan region 8 is reproduced. The display may be embodied as an LCD display. The reproduction corresponds to that shown on the PC workstation 9. By looking at the display 18, the surgeon 3 can accurately orient the fluorescence scanner 1 to the scan region 8. The surgeon 3 may only be able to detect details of the fluorescence scan on the PC workstation 9 because of the respective size of the display.

In one embodiment, the fluorescence scanner 1 includes a control device (not shown in any greater detail) which has a distance checking indicator 19 integrated into the display 18. The distance checking indicator 19 indicates a predetermined distance between the fluorescence scanner 1 and the scan region 8. The predefined distance is produced based on the focal distance of the imaging optics of the fluorescence scanner 1 and represents that distance at which, within the limits of the optical quality of the imaging optics, the greatest possible image sharpness for images of the scan region 8 is able to be achieved.

In one embodiment, the distance checking indicator 19 may include a display element, which is integrated on the display 18, into the presentation of the fluorescence scan or of the area of scan region 8. For example, a presentation element highlighted in color, for example, a circle, a cross-hair, or a bar, may be included on the presentation of the fluorescence scan. The presentation element turns a particular color, for example, green, if the predetermined distance is maintained. In one embodiment, the distance checking indicator 19 includes an additional indicator, such as an LED, which is arranged to shine through, behind, or near the display 18 in the distance checking indicator 19. In this embodiment, by illuminating in a specific color or by changing its color, the additional indicator indicates the maintenance or non-maintenance of the predefined distance.

Figure 2:
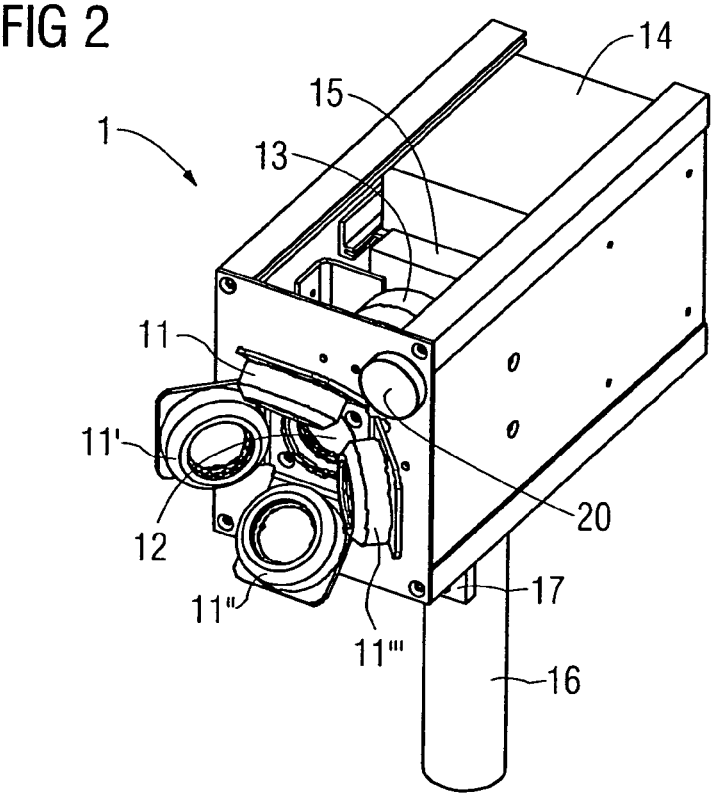
FIG. 2 is a perspective view that illustrates one embodiment of a fluorescence scanner with its housing opened at the top.

FIG. 2 is a perspective view of one embodiment of a fluorescence scanner 1. The top cover of the housing is omitted from FIG. 2. In one embodiment, as shown in FIG. 2, the fluorescence scanner 1 includes a handle 16 which can be held by the surgeon 3. A switch 17 is disposed on the handle 16. The switch 17 allows the surgeon 3 to manually actuate a fluorescence scan.

In one embodiment, the fluorescence scanner 1 includes excitation light sources 11, 11'', 11'', 11''' that are arranged in the front area, which is opposite the distance checking indicator 19, so that they can illuminate an area approximately 6 to 10 cm away from the unit. The excitation light sources 11, 11', 11'', 11''' are arranged at an angle of around 45° with respect to the front panel. This embodiment may produce an optimum working distance, for example, no contact is to be made with the scan region 8 and the distance from the scanner 1 to the scan region 8 does not demand too high of excitation light intensity.

In one embodiment, the excitation light sources 11, 11', 11'', 11''' are based on Halogen lighting media. In another embodiment, the excitation light sources 11, 11', 11'', 11''' are based on LEDs (Light Emitting Diodes) because Halogen lighting media is not generally able to be operated with short switching times. Since an individual LED has a comparatively low luminous intensity, each of the excitation light sources 11, 11', 11'', 11''' includes an LED array that has around 60 LEDs. Each of the total of four LED arrays has an overall light output of around 0.25 to 1 Watt.

In one embodiment, the fluorescence scanner 1 includes a lens 12 that is aligned toward the front. Fluorescent light and also normal light and ambient light reach the fluorescence scanner 1 through the lens 12. The lens 12 implements a specific focal distance of the imaging optics, for example, a distance at which the greatest image sharpness is obtained. In one embodiment, the focal distance is of an order of magnitude of between 1 and 40 cm.

In one embodiment, the depth of field, that is the focal distance range within which images with high image sharpness are able to be detected, is predetermined by the lens 12 in combination with the shutter to be set by the construction, or if necessary by an adjustable shutter. In one embodiment, an adjustable shutter includes an iris or leaf shutter. If an adjustable shutter is not provided, the shutter opening is provided by the radial restriction of the beam entry of the imaging optics, especially through the mounting of the lens 12 as well as by the front-side opening of the fluorescence scanner 1, through which the beam path passes. Because of the normally low luminous intensity of the fluorescence to be detected, a large aperture is usually provided which causes an increase in the light intensity, but brings with it a reduction in the depth of field.

In one embodiment, the control device includes a distance sensor 20 arranged on the front of the fluorescence scanner 1. In this embodiment, the adherence to the focal distance predetermined by the imaging optics is able to be checked. The distance sensor 20 may be embodied as an IR sensor. In an alternative embodiment, the distance sensor 20 may be embodied as a laser, ultrasound or radar sensor. The distance between target scan region 8 and fluorescence scanner 1 is measured using the distance sensor 20. The distance sensor 20 measures distances of the order of magnitude of the focal distance of the imaging optics. Depending on the measured distance and the focal distance of the imaging optics, the distance checking indicator 19 is activated.

In one embodiment, the incident light passes through a filter 13 after the lens 12. In this embodiment, the fluorescent light is not outshone by the ambient light. In one embodiment, the filter 13 only allows light in the wavelength range of the fluorescence to pass through it, for example, during a fluorescence scan. In one embodiment, a filter changer (not shown in any greater detail in the Figures) removes the filter from the path of the beam so that light in the visible wavelength can pass through. In this embodiment, an image in the visible wavelength area may be recorded. Depending on the optical characteristics of the overall construction, the filter can be omitted for recording on the basis of visible light or, alternatively, another filter can be placed (swapped), for example, by the filter changer, into the path of the beam. In one embodiment, the filter changer may include a hinged flap or rotation mechanism.

In one embodiment, light that passes through the filter 13 reaches the image detector. The image detector is based on a digital technology and may be embodied as a CCD camera. The CCD camera 15 is able to record images both in the wavelength range of visible light and also in the wavelength range of fluorescence. The image data recorded by the CCD camera 15 is received by a data recording unit. The data recording unit wirelessly transmits the image data to external equipment. The data recording unit 14 may include a memory that stores scanned images. The scanned images can be either used by default or only used if a data connection to outside equipment is not available.

In one mode of operation, the fluorescence scanner 1 is initially operated such that normal images are recorded in the visible wavelength range; for example, either no filter 13 or a filter 13 which lets the visible light pass through it is arranged in the path of the beam. The surgeon 3 initiates a fluorescence scan by pressing the switch 17 after he has aimed the device at the region of the body 8 in question, which he can do with the aid of the recorded optical image. The current image in the visible wavelength range is stored. A filter 13, which only allows light in the fluorescent wavelength range to pass through it, is then arranged (swapped) in the path of the beam. The excitation light sources 11, 11', 11", 11''' are activated and a fluorescence scan is stored. This sequence, if it is undertaken sufficiently quickly, allows the storage of an optical and a fluorescence recording to be achieved essentially with a matching angle of view, which can then be superimposed over each other. The superimposition (fusion) can also be supported by an algorithm which can compensate automatically for slight deviations in the image position.

In one embodiment, the control device, which includes the distance sensor 20 and the distance checking indicator 19, is integrated into the data recording unit 14. The control device can, for example, be embodied as a software control or can be hard-wired as a hardware module, for example, as an ASIC (Application Specific Integrated Circuit), as a CMOS circuit or another suitable electronic circuit.

The control device uses the distance sensor 20 to record the distance to the scan region 8, in order to support maintenance of a distance which matches the focal distance of the imaging optics. In one exemplary embodiment, the surgeon 3 can check the distance by checking the distance checking indicator 19 and only actuating a fluorescence scan if the correct distance is maintained. In another exemplary embodiment, the distance is checked automatically by the control device with the initiation of a fluorescence scan by the surgeon 3 only being enabled if the correct distance is maintained. In this exemplary embodiment, despite the switch 17 being pressed, no scan is initiated. In another exemplary embodiment, a fluorescence scan is initiated by the control device as soon as the surgeon 3 has pressed the switch 17 and the correct distance has been set. In this embodiment the actual initiation of the scan can thus also actually be undertaken after a delay once the switch 17 has been pressed, namely at the point at which the correct distance is set after the switch 17 is pressed.

In another exemplary embodiment, the scanner 1 operates in a pulsed operation, in which not just a single image is recorded, but an automatically pulsed series of a plurality of images are recorded. In this embodiment, an individual pulse, which records an individual image, is only triggered by the control device when the correct distance is maintained. The pulse sequence can be initiated, however, by pressing the switch 17, for example, once or continuously.

In one embodiment, the recording of an image is initiated independently of maintaining the correct distance whenever the switch 17 is pressed in pulsed operation at each pulse. However, the individually recorded images are marked by the control device depending on the respective distance, so that it is possible to recognize afterwards which images have been recorded at the correct distance. It is then, for example, possible to discard images recorded at an unsuitable distance, not to display them or not to store them. This embodiment makes it possible to evaluate images in accordance with the degree of adherence to the correct distance. In this embodiment, a better evaluated image can be used in each case, but a slightly less well evaluated image can be rejected.

FIG. 3 is a side view of the fluorescence scanner 1. In one embodiment, as shown in FIG. 3, the fluorescence scanner 1 includes a handle 16, a switch 17, and excitation light sources 11, 11", 11''' arranged on the front of the housing. As shown in FIG. 3, the excitation light sources 11, 11" are set at an angle of around 45° in relation to the housing.

The distance sensor 20 can be seen on the front of the fluorescence scanner 1. A dashed arrow indicates that the distance sensor 20 measures a distance on the front of the fluorescence scanner 1. In one embodiment, the distance sensor 20 is disposed so that the distance between the fluorescence scanner 1 and the scan region (not shown here) can be measured.

In one embodiment, as shown in FIG. 3, the display 18 is arranged on the back of the fluorescence scanner 1. However, the fluorescence scanner 1 can, depending on the area in which it is to be used and to reduce the costs, also be embodied without the display 18.

In one embodiment, as shown in FIG. 3, the distance checking indicator 19 is arranged on the back of the fluorescence scanner 1. The distance checking indicator 19 may be integrated into the display 18 or independent of it. The distance checking indicator allows a surgeon 8 to keep an eye on the distance checking indicator 19 when creating a fluorescence scan. In one embodiment, the distance checking indicator 19 is disposed on the back of the unit. The back of the unit is a suitable location for the checking indicator 19 because the fluorescence scanner 1 is generally held close to the scan region 8. In one embodiment, the distance checking indicator 19 is disposed on a side or on the top of the fluorescence scanner 1.

In alternative embodiments, instead of a distance checking light 19, a mechanical (vibration) or acoustic (buzzer) indicator can be provided. In one embodiment, the distance indication can be dispensed with entirely if the checking of the scan triggering is undertaken automatically as a function of maintaining the relevant distance.

One embodiment of the invention can be summarized as follows. An optical scanning device includes an excitation light source with an image detector, and with imaging optics that dictate a focal distance, which, when maintained can detect a scan image with the greatest image sharpness. In one embodiment, the scanning device features a control device that includes a distance sensor through which the distance between the optical scanning device and the object to be scanned can be measured. A maintenance of the focal distance as a function of the measured distance is able to be checked by a control device. The checking of the maintenance of the focal distance by the control device can assist the user in a recording scan images with high image sharpness. In a further embodiment, the control device can suppress a triggering of the detection of a scan image or a storage of a scan image. In a further embodiment, the control device includes a distance checking indicator by which the maintenance of the correct focal distance can be displayed. In a further embodiment, the scanning device is embodied as a fluorescence scanner.

The invention claimed is:

1. An optical scanning device for scanning an object, the device comprising:
    an excitation light source operable to illuminate the object to be scanned;
    an image detector operable to detect excited emission rays through illumination of the object to be scanned by the excitation light source and includes imaging optics that dictate a focal distance;
    a distance checking indicator;
    a distance sensor operable to measure a distance between the optical scanning device and the object to be scanned; and
    a control device that is operable to activate the distance checking indicator when the control device determines, as a function of the measured distance, that the image detector is positioned at or near the focal distance.

2. The optical scanning device as claimed in claim 1, wherein the control device is operable to suppress a triggering of the detection of a scan image.

3. The optical scanning device as claimed in claim 1, wherein the control device is operable to suppress a storage of a scan image.

4. The optical scanning device as claimed in claim 1, wherein the distance checking indicator includes a light emitter.

5. The optical scanning device as claimed in claim 1, wherein the display that includes the distance checking indicator is on the optical scanning device.

6. The optical scanning device as claimed in claim 1, wherein the distance sensor includes an IR sensor.

7. The optical scanning device as claimed in claim 1, wherein the image detector is operable to detect emission radiation of the object to be scanned.

8. The optical scanning device as claimed in claim 7, wherein the image detector is operable to detect emission radiation of the object to be scanned in the wavelength range of luminescence light.

9. The optical scanning device as claimed in claim 7, wherein the image detector is operable to detect radiation of the object to be scanned in the wavelength range of fluorescence light.

10. The optical scanning device as claimed in claim 4, wherein the light emitter comprises an LED.

11. The optical scanning device as claimed in claim 1, wherein the control device comprises a software control, a hardware module, an ASIC (Application Specific Integrated Circuit), or a CMOS circuit.

12. The optical scanning device as claimed in claim 2, wherein the control device is operable to suppress the detection of the scan image after checking and determining that the measured distance is not a predetermined distance.

13. The optical scanning device as claimed in claim 2, wherein the control device includes a distance checking indicator of a display, the distance checking indicator being activated by the control device.

14. The optical scanning device as claimed in claim 3, wherein the control device includes a distance checking indicator of a display, the distance checking indicator activated by the control device.

15. The optical scanning device as claimed in claim 1 wherein the image detector is operable to detect a scan image of the emission radiation of the object to be scanned with a highest level of image sharpness at the focal distance.

16. The optical scanning device as claimed in claim 8 wherein the wavelength range is 750 nm to 900 nm.

17. The optical scanning device as claimed in claim 8 wherein the wavelength range is 760 nm to 800 nm.

18. A hand-held medical optical scanning device for scanning a patient during a medical operation, the medical optical scanning device comprising:
    an excitation light source operable to illuminate the patient to be scanned;
    an image detector operable to detect excited emission rays through illumination of the patient, the image detector includes imaging optics that dictate a focal distance from the patient;
    a distance sensor operable to measure a distance between the optical scanning device and the patient; and
    a control device that is operable to stop detecting excited emission rays when the control device determines, as a function of the measured distance, that the image detector is not positioned at or near the focal distance.

19. The hand-held medical optical scanning device of claim 18, wherein the excitation light source, image detector, distance sensor and control device are mobile devices that are battery-operated.

20. The hand-held medical optical scanning device of claim 18, wherein the optical scanning device is a fluorescence scanner.

* * * * *